(12) United States Patent
Haddad et al.

(10) Patent No.: US 7,727,710 B2
(45) Date of Patent: Jun. 1, 2010

(54) MATERIALS, METHODS, AND KITS FOR REDUCING NONSPECIFIC BINDING OF MOLECULES TO A SURFACE

(75) Inventors: Louis C. Haddad, Mendota Heights, MN (US); Barbara C. Swenson, North St. Paul, MN (US); Catherine A. Bothof, Stillwater, MN (US); Madhusudan Raghavachari, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 823 days.

(21) Appl. No.: 10/810,738

(22) Filed: Mar. 26, 2004

(65) Prior Publication Data

US 2005/0142563 A1 Jun. 30, 2005

Related U.S. Application Data

(60) Provisional application No. 60/532,404, filed on Dec. 24, 2003.

(51) Int. Cl.
| | | |
|---|---|---|
| *C12Q 3/00* | (2006.01) | |
| *G01N 33/53* | (2006.01) | |
| *G01N 33/543* | (2006.01) | |
| *G01N 33/551* | (2006.01) | |
| *C09D 11/00* | (2006.01) | |

(52) U.S. Cl. ............... 435/4; 435/7.1; 435/962; 436/518; 436/524; 106/31.59

(58) Field of Classification Search ............ 436/518, 436/523, 528–532, 85, 119, 126, 128, 141, 436/142, 161, 162, 175, 177, 178, 825, 826, 436/824, 828, 533; 435/287.9, 803, 814, 435/815, 962, 181; 428/326, 327; 523/101; 528/290, 299, 392, 397, 401; 521/98, 131, 521/132, 84.1, 102, 109.1, 121, 139, 138, 521/911, 30, 53; 516/31, 201, 25–29; 536/29.13; 524/723, 704, 462, 17; 514/601; 564/80, 564/82, 88, 96, 98; 554/94, 150, 231; 106/170.45; 257/40, 642, 643, 787–789; 438/49, 115, 438/127, 458, 471–477, 654, 677, 759, 780; 427/259; 210/500.38, 500.41, 502.1, 503, 210/504, 505, 506, 508
See application file for complete search history.

(56) References Cited

U.S. PATENT DOCUMENTS

| | | | | | |
|---|---|---|---|---|---|
| 3,356,628 | A | * | 12/1967 | Smith et al. | ............ 524/544 |
| 3,654,244 | A | * | 4/1972 | Pittman et al. | ............ 526/243 |
| 3,686,355 | A | * | 8/1972 | Gaines et al. | ............ 264/341 |
| 4,153,661 | A | | 5/1979 | Ree et al. | |
| 4,240,751 | A | * | 12/1980 | Linnecke et al. | ............ 356/409 |
| 4,373,519 | A | | 2/1983 | Errede et al. | |
| 4,399,235 | A | | 8/1983 | Raley, Jr. et al. | |
| 4,460,642 | A | | 7/1984 | Errede et al. | |
| 4,483,920 | A | | 11/1984 | Gillespie et al. | |
| 4,539,256 | A | | 9/1985 | Shipman | |
| 4,565,663 | A | | 1/1986 | Errede et al. | |
| 4,596,723 | A | * | 6/1986 | Kaufman et al. | ............ 427/336 |
| 4,619,897 | A | | 10/1986 | Hato et al. | |
| 4,726,989 | A | | 2/1988 | Mrozinski | |
| 4,737,560 | A | | 4/1988 | Heilmann et al. | |
| 4,757,014 | A | | 7/1988 | Hendrickson et al. | |
| 4,780,367 | A | | 10/1988 | Lau et al. | |
| 4,810,381 | A | | 3/1989 | Hagen et al. | |
| 4,839,296 | A | | 6/1989 | Kennedy et al. | |
| 4,855,234 | A | | 8/1989 | Hendrickson et al. | |
| 4,906,378 | A | | 3/1990 | Hagen et al. | |
| 4,923,978 | A | | 5/1990 | McCormick | |
| 4,954,444 | A | | 9/1990 | Eveleigh et al. | |
| 4,957,943 | A | | 9/1990 | McAllister et al. | |
| 4,971,736 | A | | 11/1990 | Hagen et al. | |
| 5,010,183 | A | | 4/1991 | Macfarlane | |
| 5,011,861 | A | | 4/1991 | Coull et al. | |
| 5,015,373 | A | | 5/1991 | Carr et al. | |
| 5,019,232 | A | | 5/1991 | Wilson et al. | |
| 5,030,697 | A | | 7/1991 | Hugl et al. | |
| 5,071,610 | A | | 12/1991 | Hagen et al. | |

(Continued)

FOREIGN PATENT DOCUMENTS

EP 0 281 368 A 9/1988

(Continued)

OTHER PUBLICATIONS

3M™, NOVEC™ Fluorosurfactants for paints and coatings, Application Information, available at <http://www.3m.com> (retrieved Mar. 29, 2007).*

(Continued)

*Primary Examiner*—Unsu Jung
*Assistant Examiner*—Leon Y. Lum
(74) *Attorney, Agent, or Firm*—Julie A. Lapos-Kuchar; Dena M. Ehrich

(57) ABSTRACT

The present invention provides materials, methods, and kits for reducing nonspecific binding of molecules to a surface, particularly in a solid phase material, and more specifically a solid phase material that includes a hydrophobic portion, by contacting the solid phase material with a fluorinated nonionic surfactant comprising two or more fluorinated hydrophobic segments and one or more hydrophilic segments.

13 Claims, No Drawings

U.S. PATENT DOCUMENTS

| | | | |
|---|---|---|---|
| 5,077,210 A * | 12/1991 | Eigler et al. ............... 435/176 |
| 5,079,155 A | 1/1992 | Cox et al. |
| 5,108,597 A | 4/1992 | Funkenbusch et al. |
| 5,141,634 A | 8/1992 | Carr et al. |
| 5,147,539 A | 9/1992 | Hagen et al. |
| 5,182,016 A | 1/1993 | Funkenbusch et al. |
| 5,183,705 A | 2/1993 | Birkholz et al. |
| 5,187,066 A | 2/1993 | Becker et al. |
| 5,187,083 A | 2/1993 | Mullis |
| 5,200,471 A | 4/1993 | Coleman et al. |
| 5,205,929 A | 4/1993 | Carr et al. |
| 5,207,915 A | 5/1993 | Hagen et al. |
| 5,229,163 A * | 7/1993 | Fox ............... 204/169 |
| 5,234,809 A | 8/1993 | Boom et al. |
| 5,238,621 A | 8/1993 | Hagen et al. |
| 5,264,184 A | 11/1993 | Aysta et al. |
| 5,268,307 A * | 12/1993 | Breillatt et al. ............... 436/528 |
| 5,271,833 A | 12/1993 | Funkenbusch et al. |
| 5,279,742 A | 1/1994 | Markell et al. |
| 5,294,668 A | 3/1994 | Babu |
| 5,328,758 A | 7/1994 | Markell et al. |
| 5,334,316 A | 8/1994 | Bruening et al. |
| 5,344,701 A | 9/1994 | Gagnon et al. |
| 5,346,619 A | 9/1994 | Funkenbusch et al. |
| 5,380,901 A | 1/1995 | Antonucci et al. |
| RE34,910 E | 4/1995 | Funkenbusch et al. |
| 5,405,951 A | 4/1995 | Woodard |
| 5,415,779 A | 5/1995 | Markell et al. |
| 5,438,127 A | 8/1995 | Woodard et al. |
| 5,438,128 A | 8/1995 | Nieuwkerk et al. |
| 5,438,129 A | 8/1995 | Woodard et al. |
| 5,451,453 A | 9/1995 | Gagnon et al. |
| 5,464,541 A | 11/1995 | Aysta et al. |
| 5,472,600 A | 12/1995 | Ellefson et al. |
| 5,486,358 A | 1/1996 | Coleman et al. |
| 5,491,083 A * | 2/1996 | Arentzen et al. ............... 435/181 |
| 5,510,084 A | 4/1996 | Cros et al. |
| 5,525,319 A | 6/1996 | Woodard et al. |
| 5,543,305 A | 8/1996 | Cummins et al. |
| 5,585,236 A | 12/1996 | Bonn et al. |
| 5,595,649 A | 1/1997 | Markell et al. |
| 5,610,287 A | 3/1997 | Nikiforov et al. |
| 5,620,663 A | 4/1997 | Aysta et al. |
| 5,620,852 A | 4/1997 | Lin et al. |
| 5,625,053 A | 4/1997 | Kresheck et al. |
| 5,633,290 A | 5/1997 | Frechet et al. |
| 5,635,060 A | 6/1997 | Hagen et al. |
| 5,637,687 A | 6/1997 | Wiggins |
| 5,639,372 A | 6/1997 | Hagen et al. |
| 5,688,370 A | 11/1997 | Hagen et al. |
| 5,691,208 A | 11/1997 | Miltenyi et al. |
| 5,702,610 A | 12/1997 | Hagen et al. |
| 5,709,943 A | 1/1998 | Coleman et al. |
| 5,738,790 A | 4/1998 | Hagen et al. |
| 5,741,828 A | 4/1998 | Stoy et al. |
| 5,786,208 A | 7/1998 | Clark et al. |
| 5,801,237 A | 9/1998 | Johansson |
| 5,804,684 A | 9/1998 | Su |
| 5,834,583 A | 11/1998 | Hancock et al. |
| 5,882,521 A | 3/1999 | Bouvier et al. |
| 5,904,848 A | 5/1999 | Wong et al. |
| 5,919,626 A | 7/1999 | Shi et al. |
| 5,976,367 A | 11/1999 | Bouvier et al. |
| 5,976,468 A | 11/1999 | Godec et al. ............... 422/100 |
| 5,993,935 A | 11/1999 | Rasmussen et al. |
| 5,997,818 A | 12/1999 | Hacker et al. |
| 5,999,935 A | 12/1999 | Clark et al. |
| 6,007,690 A | 12/1999 | Nelson et al. |
| 6,048,457 A | 4/2000 | Kopaciewicz et al. |
| 6,048,550 A | 4/2000 | Chan et al. |
| 6,063,838 A | 5/2000 | Patnode et al. |
| 6,068,751 A | 5/2000 | Neukermans et al. |
| 6,071,406 A | 6/2000 | Tsou |
| 6,074,827 A | 6/2000 | Nelson et al. |
| 6,074,927 A | 6/2000 | Kepler et al. |
| 6,084,091 A | 7/2000 | Müller et al. |
| 6,093,559 A | 7/2000 | Bookbinder et al. |
| RE36,811 E | 8/2000 | Markell et al. |
| 6,103,199 A | 8/2000 | Bjornson et al. |
| 6,200,474 B1 | 3/2001 | Kopaciewicz et al. |
| 6,207,251 B1 | 3/2001 | Balsimo et al. |
| 6,254,780 B1 | 7/2001 | Bouvier et al. |
| 6,261,497 B1 | 7/2001 | Wong et al. |
| 6,265,168 B1 | 7/2001 | Gjerde et al. |
| 6,265,224 B1 | 7/2001 | Collis et al. |
| 6,277,488 B1 | 8/2001 | Kobe et al. |
| 6,284,113 B1 | 9/2001 | Bjornson et al. |
| 6,306,273 B1 | 10/2001 | Wainright et al. |
| 6,319,469 B1 | 11/2001 | Mian et al. |
| 6,344,326 B1 | 2/2002 | Nelson et al. |
| 6,383,783 B1 | 5/2002 | Haddad |
| 6,428,707 B1 | 8/2002 | Berg et al. |
| 6,450,047 B2 | 9/2002 | Swedberg et al. |
| 6,451,260 B1 | 9/2002 | Düsterhoft et al. |
| 6,479,300 B1 | 11/2002 | Jiang et al. |
| 6,503,564 B1 * | 1/2003 | Fleming et al. ............... 427/255.6 |
| 6,532,997 B1 | 3/2003 | Bedingham et al. |
| 6,537,502 B1 | 3/2003 | Shukla et al. |
| 6,617,136 B2 | 9/2003 | Parthasarathy et al. |
| 6,632,399 B1 | 10/2003 | Kellogg et al. |
| 6,653,151 B2 * | 11/2003 | Anderson et al. ............... 506/32 |
| 6,664,104 B2 | 12/2003 | Pourahmadi et al. |
| 6,664,354 B2 | 12/2003 | Savu et al. |
| 6,692,596 B2 | 2/2004 | Moll et al. |
| 6,720,187 B2 | 4/2004 | Bedingham et al. |
| 6,723,236 B2 | 4/2004 | Fisk et al. |
| 6,730,516 B2 | 5/2004 | Jedrzejewski et al. |
| 6,734,401 B2 | 5/2004 | Bedingham et al. |
| 6,780,818 B2 | 8/2004 | Gundel et al. |
| 2002/0046966 A1 | 4/2002 | Muscate-Magnussen |
| 2002/0048533 A1 | 4/2002 | Harms et al. |
| 2002/0064885 A1 | 5/2002 | Bedingham et al. |
| 2002/0155034 A1 | 10/2002 | Perman et al. |
| 2002/0182114 A1 | 12/2002 | Ingenhoven et al. |
| 2003/0011092 A1 | 1/2003 | Tan et al. |
| 2003/0017567 A1 | 1/2003 | Parthasarathy et al. |
| 2003/0018177 A1 | 1/2003 | Haddad |
| 2003/0053934 A1 | 3/2003 | Andersson et al. |
| 2003/0062310 A1 | 4/2003 | Zare et al. |
| 2003/0120062 A1 | 6/2003 | Parthasarathy et al. |
| 2003/0138779 A1 | 7/2003 | Parthasarathy et al. |
| 2003/0139549 A1 | 7/2003 | Savu et al. |
| 2003/0139550 A1 | 7/2003 | Savu et al. |
| 2003/0155034 A1 | 8/2003 | De Beukeleer et al. |
| 2003/0228701 A1 | 12/2003 | Wong et al. |
| 2003/0228706 A1 | 12/2003 | Ramstad et al. |
| 2004/0016702 A1 | 1/2004 | Hennessy et al. |
| 2004/0018116 A1 | 1/2004 | Desmond et al. |
| 2004/0018559 A1 | 1/2004 | Lau et al. |

FOREIGN PATENT DOCUMENTS

| | | |
|---|---|---|
| EP | 0 309 259 A2 | 3/1989 |
| EP | 0 389 063 A2 | 9/1990 |
| EP | 0 409 432 A2 | 1/1991 |
| EP | 0 426 488 A1 | 5/1991 |
| EP | 0 447 362 A1 | 9/1991 |
| EP | 0 524 864 A1 | 1/1993 |
| EP | 0 572 907 A2 | 12/1993 |
| EP | 0 309 259 B1 | 6/1994 |
| EP | 0 426 488 B1 | 4/1997 |
| EP | 0770689 A2 | 5/1997 |
| EP | 0 389 063 B1 | 8/1997 |
| EP | 0 524 864 B1 | 5/1998 |

| | | |
|---|---|---|
| EP | 0 897 978 A2 | 2/1999 |
| GB | 857689 * | 1/1961 |
| JP | 2-268-682 | 11/1990 |
| JP | 2-295-485 | 12/1990 |
| JP | 7-265718 | 10/1995 |
| JP | 9-302-034 | 11/1997 |
| WO | WO 90/10637 A1 | 9/1990 |
| WO | WO 92/18514 A1 | 10/1992 |
| WO | WO 94/00464 A1 | 1/1994 |
| WO | WO 95/19781 A | 7/1995 |
| WO | WO 95/24505 A1 | 9/1995 |
| WO | WO 97/07239 A1 | 2/1997 |
| WO | WO 97/21090 A | 6/1997 |
| WO | WP 97/27325 A2 | 7/1997 |
| WO | WO 98/04909 A1 | 2/1998 |
| WO | WO 99/40174 A1 | 8/1998 |
| WO | WO 99/15876 A1 | 4/1999 |
| WO | WO 99/15888 A1 | 4/1999 |
| WO | WO 99/22021 A1 | 5/1999 |
| WO | WO 99/23487 A1 | 5/1999 |
| WO | WO 99/28504 A1 | 6/1999 |
| WO | WO 99/39120 A1 | 8/1999 |
| WO | WO 99/46591 A2 | 9/1999 |
| WO | WO 00/45180 A1 | 8/2000 |
| WO | WO 00/62051 A2 | 10/2000 |
| WO | WO 00/68336 A1 | 11/2000 |
| WO | WO 01/03149 A1 | 1/2001 |
| WO | WO 01/12327 A | 2/2001 |
| WO | WO 01/21632 A1 | 3/2001 |
| WO | WP 01/25490 A1 | 4/2001 |
| WO | WO 01/30873 A1 | 5/2001 |
| WO | WO 01/30995 A | 5/2001 |
| WO | WO 01/37291 A1 | 5/2001 |
| WO | WO 01/38516 A1 | 5/2001 |
| WO | WO 01/38865 A1 | 5/2001 |
| WO | WO 01/68240 A2 | 9/2001 |
| WO | WO 01/68913 A2 | 9/2001 |
| WO | WO 01/71732 A2 | 9/2001 |
| WO | WO 02/44400 A2 | 6/2002 |
| WO | WO 03/058224 A1 | 7/2003 |
| WO | WO 2004/009851 A2 | 1/2004 |
| WO | WO 2004/010760 A2 | 2/2004 |
| WO | WO 2004/011141 A1 | 2/2004 |
| WO | WO 2004/011142 A1 | 2/2004 |
| WO | WO 2004/011592 A2 | 2/2004 |
| WO | WO 2004/011681 A1 | 2/2004 |
| WO | WO 2005/005045 A | 1/2005 |

OTHER PUBLICATIONS

3M™, NOVEC™ Fluorosurfactant FC-4432, Product Information, available at <http://www.3m.com> (retrieved Mar. 29, 2007).*
3M™, NOVEC™ Fluorosurfactant FC-4432, Material Safety Data Sheet, available at <http://www.3m.com> (retrieved Mar. 29, 2007).*
Emmer Asa et al.; "Wall deactivation with fluorosurfactants for capillary electrophoretic analysis of biomolecules" *Electroophoresis*, vol. 22, No. 4, Feb. 2001; pp. 660-665, XP002325650; ISSN: 0173-0835, p. 664.
Yamaguchi Y et al. "*Increased Sensitivity for Detection of Human Cytomegalovirus in Urine by Removal of Inhibitors for the Polymerase Chain Reaction*", Journal of Virological Methods, vol. 37, No. 2, 1992, pp. 209-218.
Behzadbehbahani A. et al. "*Detection of BK Virus in Urine by Polymerase Chain Reaction: A Comparison of DNA Extraction Methods*", Journal of Virological Methods, vol. 67, 1997, pp. 161-166.
"CHES buffer" datasheet [online]. Gentaur, Brussels, Belgium, [retrieved on May 24, 2007]. Retrieved from the Internet:<URL:http://www.gentaur.com/nieuwe_pagina_22.htm>; 1 page.
"CHES, Biological Buffer—Biological Buffer Compounds * 103-47-9" datasheet [online]. Sciencelab.com, Inc., Houston, TX, 1997-2005 [retrieved on May 24, 2007]. Retrieved from the Internet:<URL:http://www.sciencelab.com/page/S/PVAR/23006/SLC1912>; 1 page.
"C2885 CHES≧99% (titration)" datasheet [online]. Sigma-Aldrich Co., St. Louis, MO, 2007 [Retrieved on Jun. 5, 2007]. Retrieved from the Internet<URL:http://www.sigmaaldrich.com/catalog/search/ProductDetail/SIGMA/C2885>; 1 page.
3M Material Safety Data Sheet for FC-4430 FLUORAD™ Fluorosurfactant (9 pgs) (May 7, 2003).
3M Material Safety Data Sheet for 3M™ FLUORAD™ Fluorosurfactant FC-4432 (9 pgs) (May 21, 2003).
"ABI Prism® BigDye™ Terminators v3.0 Cycle Sequencing Kit," product information [online], Applied Biosystems, 2000, 2001 [retrieved Dec. 3, 2001]. Retrieved from the Internet: <URL:http://www.appliedbiosystems.com/products/productdetall.cfm?id=81>, p. 1.
Al-Soud et al.; "Purification and Characterization of PCR-Inhibitory Components in Blood Cells," *Journal of Clinical Microbiology*; vol. 39(2); pp. 485-493 (2001).
Altschuler et al.: "Benchmarks: Plasmid DNA Isolation Utilizing a Novel Nonionic Detergent," *BioTechniques*; vol. 17(3); pp. 434, 436 (1994).
American Society of Testing Materials, "ASTM D 570-98, Standard Test Method for Water Absorption of Plastics," *Annual Book of ASTM Standards*, pp. 31-33 and Title page (Jan. 2001).
AutoSeq98 Dye Terminator Clean-up Kit / Adapter Plate for AutoSeq96, product catalogue [online]. Amersham Biosciences, 2001 [retrieved Dec. 3, 2001]. Retrieved from the Internet: <URL:http://www.apbiotech.com/stiboasp/showmodule,asp?nModuleld=164360>, pp. 1-2.
Bartl et al.; "Simple and Broadly Applicable Preparation by Use of Magnetic Glass Particles," *Clin Chem Lab Med*, vol. 36(8), pp. 557-559 (1998).
"Blast," National Institutes of Health [online] United States, [retrieved Oct. 23, 2000]. Retrieved from the Internet<URL:http://www.ncbi.nlm.nih.gov/BLAST>, 2 pgs.
Bischoff et al.; "Isolation of Specific tRNAs Using an Ionic-Hydrophobic Mixed-Mode Chromatographic Matrix," *Analytical Biochemistry*; vol. 151; pp. 526-533 (1985).
QIAamp® DSP DNA Blood Mini Kit Handbook, 28 pages (Jan. 2004).
Boom et al., "Rapid and Simple Method for Purification of Nucleic Acids," *Journal of Clinical Microbiology*, Mar. 1990; vol. 28, No. 3; pp. 495-503, Publication page, and Title page.
Breadmore et al.; "Microchip-Based Purification of DNA from Biological Samples," *Analytical Chemistry*; vol. 75(8); pp. 1880-1886 (2003).
Brezinski; "Laying the foundation for New Technologies 3M Creates a new building block for its fluorosurfactants," *Paintings and Coatings Industry*, (Jan. 2003).
Buffone et al.; "Isolation of DNA from Biological Specimens without Extraction with Phenol," *Clinincal Chemistry*, vol. 31(1), pp.164-165 (1985).
Burckhardt; "Amplification of DNA From Whole Blood," PCR Methods and Applications, *Cold Spring Harbor Laboratory Press*, vol. 3, No. 4., pp. 239-243 (Feb. 1994).
Rudbeck et al.; "Benchmarks: Rapid, Simple Alkaline Extraction of Human Genomic DNA from Whole Blood, Buccal Epithelial Cells, Semen and Forensic Stains for PCR." *BioTechniques*, vol. 25(4), pp. 588-589, 592 (1998).
Fraker at al., *Biochem. Biophys. Res. Commun.*, vol. 80, pp. 849-857 (1978).
Huber et al.; "High-performance liquid chromatographic separation of detrilyated oligonucleotides on highly cross-linked poly-(styrene-divinylbenzene) particles," *Journal of Chromatography*, vol. 599; pp. 113-118 (1992).
Jeffreys, et al., "DNA 'Fingerprints' and Segregation Analysis of Multiple Markers in Human Pedigrees," *American Journal of Human Genetics*, vol. 39, pp. 11-24 (1986).
Kogan et al.; "An Improved Method for Prenatal Diagnosis of Genetic Diseases by Analysis of Amplified DNA Sequences, Application to Hemophilia A," *New England Journal of Medicine*, vol. 317, pp. 985-990 (1987).

Nielsen et al.; "Peptide nucleic acid (PNA), a DNA mimic with a pseudopetide backbone." *Chemical Society Review*, vol. 26; pp. 73-78 (1997).

Tian et al; "Evaluation of Silica Resins for Direct and Efficient Extraction of DNA from Complex Biological Matrices in a Miniaturized Format," *Analytical Biochemistry*, vol. 283, pp. 175-191 (2000).

"Porex Corporate Profile," [online]. Porex Corporation, 2001 [retrieved Dec. 5, 2001]. Retrieved from the Internet: <URL:http://www.porex.com/english/corporate/index.asp>, pp. 1-3.

"Porex Products Group," product profile [online]. Porex Corporation, 2001 [retrieved Dec. 5, 2001]. Retrieved from the Internet: <URL:http://www.porex.com/english/porous/index.asp>, pp. 1-2.

Product Information Brochure, "DuPont™ Zonyl® Fluoroadditives for Coatings Technical Information," (4 pgs) (Mar. 2003).

Product Information Brochure "3M Novec™ Fluorosurfactants FC-4430 / 3M™ Fluorad™ Fluorosurfactants are now 3M™ Novec™ Fluorosurfactants," (4 pgs), (Oct. 2003).

Product Information Brochure "Zonyl® Flurosurfactants," (2 pgs), obtained from the Internet on Dec. 1, 2003, <URL:http://web.singnet.com.sg/~paseden/dupont6.htm> (Apr. 2003).

"Purification so fast it'll make your head spin: RapTract Dye Terminator Removal Kit," Prollnx Product Information, Bothell, WA, 2000. pp. 1-6.

"3M Empore Products 96-Well Plates," product listing [online]. 3M Corporation, 1999 [retrieved Dec. 5, 2001]. Retrieved from the Internet: <Url:http://www.mmm.com/empore/formats/Plates/sorbavlb/index.htm>, pp. 1-2.

"3M Empore Products Empore 96-Well Plates" SPE Extraction Disk Plates & Filter Plates, 3M Extraction Disk Plates for SPE, product listing [online]. 3M Corporation, 1999 [retrieved Dec. 5, 2001]. Retrieved from the Internet: <URL:http://www.mmm.com/empore/formats/Plates/index.htm>, pp. 1-2.

Takeuchi et al., "Ion Chromatography Using Anion Exchangers Modified with Anionic Polysaccharides," LCGC Magazine [online]. LCGC North America, 2001 [retrieved Oct. 2, 2001]. Retrieved from the Internet: <URL:http://www.lcgcmag.com/articles/0004_articles/0004_Takeuchi/0004 Takeuchi.asp>, pp. 1-12.

Tong, et al., "Solid-Phase Method for the Purification of DNA Sequencing Reactions," *Anal Chem*, 1992: vol. 64, No. 22: pp. 2672-2677 Publication page, and Title page.

Co-related U.S. Appl. No. 10/417,609, filed Apr. 17, 2003 entitled "Methods and Devices for Removal of Organic Molecules from Biological Mixtures Using an Anion Exchange Material that Includes a Polyoxyalkylene" (3M Case No. 58301US002).

Co-related U.S. Appl. No. 60/532,404, filed Dec. 24, 2003 entitled "Methods and Kits For Reducing Nonspecific Binding of Molecules to a Surface" (3M Case No. 59071US002).

Co-related U.S. Appl. No. 10/852,642, filed May 24, 2004 entitled "Variable Valve Apparatus and Methods" (3M Case No. 59071US003).

Co-related U.S. Appl. No. 60/532,523, filed Dec. 24, 2003 entitled "Methods for Nucleic Acid Isolation and Kits" (3M Case No. 59073US002).

Co-related U.S. Appl. No. 10/852,645, filed May 24, 2004 entitled "Methods for Nucleic Acid Isolation and Kits Using Solid Phase Material" (3M Case No. 59073US003).

Co-related U.S. Appl. No. 60/532,525, filed Dec. 24, 2003 entitled "Methods and Kits for Reducing Nonspecific Binding of Molecules to a Surface" (3M Case No. 59343US002).

Co-related U.S. Appl. No. 10/852,085, filed May 24, 2004 entitled "Methods for Nucleic Acid Isolation and Kits Using a Microfluidic Device and Concentration Step" (3M Case No. 59801US002).

Co-related U.S. Appl. No. 10/852,022, filed May 24, 2004 entitled "Methods for Nucleic Acid Isolation and Kits Using a Microfluidic Device and Sedimenting Agent" (3M Case No. 59802US002).

3M Material Safety Data Sheet FC-430 Brand Coating Additive Aug. 30, 2002.

\* cited by examiner

MATERIALS, METHODS, AND KITS FOR REDUCING NONSPECIFIC BINDING OF MOLECULES TO A SURFACE

CROSS-REFERENCE TO RELATED APPLICATIONS

The present invention claims priority to U.S. Provisional Patent Application Ser. No. 60/532,404 filed Dec. 24, 2003, which is incorporated herein by reference in its entirety.

BACKGROUND

In many biological assays, target molecules, such as polypeptides, need to be purified. This can be accomplished, for example, using affinity separations.

An affinity separation can be defined as any separation achieved by employing the specific binding of one molecule or a group of molecules by another molecule or a group of molecules. Affinity separation is used to capture an analyte (e.g., typically a macromolecule, such as a protein or nucleic acid) from a complex mixture such as serum or plasma. After capturing the analyte, the contaminants are washed away and the analyte (i.e., target molecule) is detected using well known assay protocols and/or removed from the solid phase material for further processing.

These separations can be carried out as batch processes or chromatographic processes and generally include a solid support material. Solid support materials (i.e., solid phase materials) generally suitable for affinity chromatography are well known and typically include the attachment of a ligand or binder to the carrier. Many solid support materials, however, demonstrate nonspecific binding of unwanted components such as proteins that do not have specific interactions with the ligand.

Attempts to improve on affinity supports have involved the use of an inert perfluorocarbon polymer carrier with ligands or binders attached to its surface through a highly fluorinated isocyanate anchor group (see, e.g., U.S. Pat. No. 4,954,444 (Eveleigh et al.)). Also, U.S. Pat. No. 4,619,897 (Hato et al.) discloses the immobilization of enzymes onto a fluorine resin membrane which is made hydrophilic on one side by the penetration of a perfluoroalkyl surface active agent to a prescribed depth. The asymmetrically functional membrane thus obtained is then treated with an enzyme and a crosslinking agent such as glutaraldehyde to achieve enzyme immobilization.

Because affinity separation as well as other separations involving solid supports are such powerful techniques and because currently available supports suffer from various disadvantages, there is a need for improved methods and materials, which may or may not actually function as an affinity support.

The discussion of prior publications and other prior knowledge does not constitute an admission that such material was published, known, or part of the common general knowledge.

SUMMARY

The present invention provides materials, methods, and kits for reducing nonspecific binding of molecules to a surface. More specifically, in certain embodiments, the present invention provides materials, methods, and kits for isolation of particular target molecules (e.g., polypeptides) from a sample, and more particularly for decreasing the loss of the target material due to nonspecific binding to a solid phase material.

In one embodiment, the present invention provides a method of reducing nonspecific binding of target molecules to a surface. The method includes: providing a sample that includes target molecules; providing a solid phase material that includes a hydrophobic portion and capture sites; providing a fluorinated nonionic surfactant that includes two or more fluorinated hydrophobic segments and one or more hydrophilic segments; optionally providing a secondary blocking agent; contacting the solid phase material with the fluorinated nonionic surfactant and optionally contacting the solid phase material with the secondary blocking agent to block at least a portion of the hydrophobic portion of the solid phase material (i.e., the surface involved in nonspecific binding); contacting the blocked solid phase material with the sample to adhere at least a portion of the target molecules of the sample to the capture sites; and optionally removing at least a portion of the adhered target molecules of the sample from the blocked solid phase material. The capture sites can include hydrophobically attached or covalently attached groups or molecules.

In another embodiment, the present invention provides a method of reducing nonspecific binding of target molecules to a surface. The method includes: providing a sample that includes target molecules; providing a solid phase material that includes a polytetrafluoroethylene fibril matrix and sorptive particles (i.e., particles that include the capture sites) enmeshed in the matrix; providing a fluorinated nonionic surfactant that includes two or more fluorinated hydrophobic segments and one or more hydrophilic segments; optionally providing a secondary blocking agent; contacting the solid phase material with the fluorinated nonionic surfactant and optionally contacting the solid phase material with the secondary blocking agent to block at least a portion of the polytetrafluoroethylene fibril matrix (i.e., the surface of the solid phase material involved in nonspecific binding); contacting the blocked solid phase material with the sample to adhere at least a portion of the target molecules of the biological sample to the sorptive particles; and removing at least a portion of the adhered target molecules of the sample from the blocked solid phase material.

In another embodiment, the present invention provides a method of reducing nonspecific binding of molecules to a surface. The method includes: providing a solid phase material that includes a hydrophobic portion; providing a fluorinated nonionic surfactant that includes two or more fluorinated hydrophobic segments and one or more hydrophilic segments; optionally providing a secondary blocking agent; and contacting the solid phase material with the fluorinated nonionic surfactant and optionally contacting the solid phase material with the secondary blocking agent to block at least portion of the hydrophobic portion (i.e., the surface of the solid phase material involved in nonspecific binding).

In another embodiment, the present invention provides a method of reducing nonspecific binding of target molecules to a surface. The method includes: providing a sample that includes target molecules; providing a solid phase material that includes a hydrophobic portion and one or more hydrophobically attached capture proteins; providing a fluorinated nonionic surfactant that includes two or more fluorinated hydrophobic segments and one or more hydrophilic segments; contacting the solid phase material with the fluorinated nonionic surfactant to block at least a portion of the hydrophobic portion of the solid phase material; contacting the blocked solid phase material with the sample to adhere at least a portion of the target molecules of the sample to the one or more capture proteins; and optionally removing at least a portion of the adhered target molecules of the sample from the blocked solid phase material.

In another embodiment, there is provided a method of modifying a surface. The method includes: providing a solid phase material that includes a hydrophobic portion; providing a protein and contacting the protein to the solid phase material to hydrophobically attach the protein; providing a fluorinated nonionic surfactant that includes two or more fluorinated hydrophobic segments and one or more hydrophilic segments; and contacting the solid phase material with the fluorinated nonionic surfactant to reduce nonspecific binding of other molecules to the solid phase material.

The present invention also provides kits for carrying out the various methods of the present invention.

In one embodiment, a kit includes: a solid phase material that includes a hydrophobic portion; a fluorinated nonionic surfactant that includes two or more fluorinated hydrophobic segments and one or more hydrophilic segments; an optional secondary blocking agent; and instructions for carrying out a method of the present invention. If desired, in the kit the fluorinated nonionic surfactant is disposed on the solid phase material.

In another embodiment, a kit includes: a solid phase material that includes a polytetrafluoroethylene fibril matrix and sorptive particles enmeshed in the matrix; a fluorinated nonionic surfactant that includes two or more fluorinated hydrophobic segments and one or more hydrophilic segments; an optional secondary blocking agent; and instructions for carrying out a method of the present invention.

The present invention also provides solid phase materials. In one embodiment, the present invention provides a material that includes a solid phase material having a fluorinated nonionic surfactant disposed thereon; wherein: the solid phase material includes a polytetrafluoroethylene fibril matrix and sorptive particles enmeshed in the matrix; and the fluorinated nonionic surfactant includes two or more fluorinated hydrophobic segments and one or more hydrophilic segments.

In another embodiment, the present invention provides a material that includes a solid phase material having a fluorinated nonionic surfactant disposed thereon; wherein: the solid phase material includes a thermally induced phase separation membrane; and the fluorinated nonionic surfactant includes two or more fluorinated hydrophobic segments and one or more hydrophilic segments.

In another embodiment, the present invention provides a material that includes a solid phase material having a fluorinated nonionic surfactant disposed thereon; wherein: the solid phase material includes a high internal phase emulsion foam; and the fluorinated nonionic surfactant includes two or more fluorinated hydrophobic segments and one or more hydrophilic segments.

DEFINITIONS

"Polypeptide," as used herein, refers to a polymer of amino acids and does not refer to a specific length of a polymer of amino acids. Thus, for example, the terms peptide, oligopeptide, protein, and enzyme are included within the definition of polypeptide, whether naturally occurring or synthetically derived, for instance, by recombinant techniques or chemically or enzymatically synthesized. This term also includes post-expression modifications of the polypeptide, for example, glycosylations, acetylations, phosphorylations, and the like.

"Polynucleotide" and "nucleic acid" are used interchangeably to refer to a polymeric form of nucleotides of any length, and further refer to DNA (e.g., genomic DNA, cDNA, or plasmid DNA), RNA (e.g., mRNA, tRNA, or rRNA), and PNA. It can be in a wide variety of forms, including, without limitation, double-stranded or single-stranded configurations, circular form, plasmids, relatively short oligonucleotides, peptide nucleic acids also called PNA's (as described in Nielsen et al., Chem. Soc. Rev., 26 73-78 (1997)), and the like. The nucleic acid can be genomic DNA, which can include an entire chromosome or a portion of a chromosome. The DNA can include coding (e.g., for coding mRNA, tRNA, and/or rRNA) and/or noncoding sequences (e.g., centromeres, telomeres, intergenic regions, introns, transposons, and/or microsatellite sequences). The nucleic acid can include any of the naturally occurring nucleotides as well as artificial or chemically modified nucleotides, mutated nucleotides, etc. The nucleic acid can include a non-nucleic acid component, e.g., peptides (as in PNA's), labels (radioactive isotopes or fluorescent markers), and the like.

"Isolated" refers to target molecules (i.e., target material) that have been removed from the sample in which they are originally found. This includes simply concentrating the target molecules without necessarily removing any other materials other than the original solvent in the original sample. It also includes separating the target molecules from other materials, e.g., cellular components such as lipids, salts, etc. More preferably, the isolated target molecules are substantially purified. "Substantially purified" refers to target material that is at least 50%, preferably at least 80%, and more preferably at least 95%, pure with respect to removal of a contaminant, e.g., cellular components such as lipids or salts. These percentages refer to the amount of target molecules (e.g., proteins, DNA, RNA, PNA) relative to the total amount of the target molecules and contaminants other than the solvent in the sample. Thus, the term "substantially purified" generally refers to separation of a majority of cellular components or reaction contaminants from the sample, so that compounds capable of interfering with the subsequent use of the isolated target molecules are removed.

"Adheres to" or "adherance" or "binding" refer to reversible retention via a wide variety of mechanisms, including weak forces such as Van der Waals interactions, electrostatic interactions, affinity binding, or physical trapping. The use of this term does not imply a mechanism of action, and includes adsorptive and absorptive mechanisms.

"Capture sites" refer to sites on the solid phase material to which a material adheres. Typically, the capture sites include functional groups or molecules that are either covalently attached or hydrophobically attached to the solid phase material.

"Nonspecific binding" refers to adherence of molecules to a surface of a solid phase material through a hydrophobic interaction in a manner not specified by that material's construction.

"Solid phase material" refers to a material that may include a wide variety of organic and/or inorganic materials. Such materials may be made of a polymer made of repeating units, which may be the same or different, of organic and/or inorganic compounds of natural and/or synthetic origin.

"Surfactant" refers to a substance that lowers the surface or interfacial tension of the medium in which it is dissolved.

The terms "comprises" and variations thereof do not have a limiting meaning where these terms appear in the description and claims.

As used herein, "a," "an," "the," "at least one," and "one or more" are used interchangeably and mean one or more.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention.

The description that follows more particularly exemplifies illustrative embodiments. In several places throughout the application, guidance is provided through lists of examples, which examples can be used in various combinations.

In each instance, the recited list serves only as a representative group and should not be interpreted as an exclusive list.

DETAILED DESCRIPTION OF ILLUSTRATIVE EMBODIMENTS

The present invention provides methods and kits for reducing nonspecific binding of molecules to a surface. More specifically, the methods and kits of the present invention are useful for reducing the loss of the target material due to nonspecific binding to a solid phase material. Even more specifically, the present invention provides methods for the isolation, and preferably purification and recovery, of target molecules, such as polypeptides and polynucleotides (i.e., nucleic acid), as well as small organic molecules, from a sample. Alternatively, certain methods and kits of the present invention are useful for reducing undesirable binding of molecules, which is useful in ELISA's and other immunoassays, protein blotting assays, and protein-protein interaction assays.

The solid phase material includes a hydrophobic portion and capture sites. These capture sites can be attached in a variety of ways to the solid phase material. For example, they can be covalently attached or they can be hydrophobically attached to the solid phase material. For example, if the solid phase material includes sorptive particles, these particles typically include the capture sites, which are typically provided by ligands capable of binding to (i.e., capturing) target molecules. Alternatively, if the solid phase material has no such sorptive particles hydrophobic capture molecules can be attached to the hydrophobic portion of the solid phase material through hydrophobic interactions, for example. Such hydrophobically attached molecules are typically proteins that are capable of binding to (i.e., capturing) target molecules.

It has been surprisingly discovered that the nonspecific binding of molecules (e.g., as in a target material) to a solid phase material, which includes a hydrophobic portion, can be decreased by contacting the solid phase material with a fluorinated nonionic surfactant prior to contacting the solid phase material with the sample of interest. The fluorinated nonionic surfactant includes two or more fluorinated hydrophobic segments and one or more hydrophilic segments. In certain situations, the solid phase material can also be contacted with a secondary blocking agent (e.g., a blocking protein) for further reduction in nonspecific binding. Thus, the reduction (i.e., decrease) in nonspecific binding of molecules to a surface is relative to the surface without being pretreated with the fluorinated nonionic surfactant.

Furthermore, if the capture sites are provided by capture molecules (e.g., capture proteins) hydrophobically attached to the solid phase material, it has been surprisingly discovered that the surfactant described herein does not remove such capture sites.

Materials isolated according to the invention, will be useful, for example, in assays for detection of the presence of a particular target molecule (e.g., nucleic acid or protein) in a sample. Such assays are important in the prediction and diagnosis of disease, forensic medicine, epidemiology, and public health. For example, isolated DNA may be subjected to hybridization and/or amplification to detect the presence of an infectious virus or a mutant gene in an individual, allowing determination of the probability that the individual will suffer from a disease of infectious or genetic origin. In another example, isolated antibodies or antigens can be used to diagnose disease. The ability to detect an infectious virus or a mutation in one sample among the hundreds or thousands of samples being screened takes on substantial importance in the early diagnosis or epidemiology of an at-risk population for disease, e.g., the early detection of HIV infection, cancer or susceptibility to cancer, or in the screening of newborns for diseases, where early detection may be instrumental in diagnosis and treatment. In addition, the method can also be used in basic research laboratories to isolate nucleic acid or proteins from cultured cells or biochemical reactions.

Typically, a sample containing target material (i.e., target molecules) is processed in a flow-through receptacle, although this receptacle is not a necessary requirement of the present invention.

Solid Phase Material

The solid phase material useful in the methods of the present invention may include a wide variety of organic and/or inorganic materials. Preferred materials are capable of retaining target molecules (e.g., biomolecules such as proteins). Such materials include a hydrophobic portion, which in the context of the present invention means a material that has a critical surface tension of less than the surface tension of water (e.g., less than 72 dynes/cm), and preferably less than the critical surface tension of nylon (e.g., less than 43 dynes/cm). Typically, the solid phase material includes an organic polymeric matrix.

The solid phase material is preferably dried to a generally stable moisture content. It is typically then stored dry to maintain that stable moisture content.

Generally suitable materials are chemically inert, physically and chemically stable, and compatible with a variety of biological samples. Examples of suitable polymers include, for example, polyolefins and fluorinated polymers. The solid phase material is typically washed to remove salts and other contaminants prior to use. The solid phase material is preferably used in a flow-through receptacle, for example, such as a pipet, syringe, or larger column, microtiter plate, or microfluidic device, although suspension methods that do not involve such receptacles could also be used.

The solid phase material useful in the methods of the present invention can include a wide variety of materials in a wide variety of forms. For example, it can be in the form of particles or beads, which may be loose or immobilized, fibers, foams, frits, microporous films, membranes, or a substrate with microreplicated surface(s). If the solid phase material includes particles, they are preferably uniform, spherical, and rigid to ensure good fluid flow characteristics.

For flow-through applications of the present invention, such materials are typically in the form of a loose, porous network to allow uniform and unimpaired entry and exit of large molecules and to provide a large surface area. Preferably, for such applications, the solid phase material has a relatively high surface area, such as, for example, more than one meter squared per gram ($m^2/g$). For applications that do not involve the use of a flow-through device, the solid phase material may or may not be in a porous matrix. Thus, membranes can also be useful in certain methods of the present invention.

For applications that use particles or beads, they may be introduced to the sample or the sample introduced into a bed of particles/beads and removed therefrom by centrifuging, for example. Alternatively, particles/beads can be coated (e.g., pattern coated) onto an inert substrate (e.g., polycarbonate or polyethylene), optionally coated with an adhesive, by a variety of methods (e.g., spray drying). If desired, the substrate can be microreplicated for increased surface area and enhanced clean-up. It can also be pretreated with oxygen plasma, e-beam or ultraviolet radiation, heat, or a corona treatment process, for example. This substrate can be used, for example, as a cover film, or laminated to a cover film, on a reservoir in a microfluidic device.

In one embodiment, the solid phase material includes a fibril matrix, which may or may not have particles enmeshed therein. The fibril matrix can include any of a wide variety of fibers. Typically, the fibers are insoluble in an aqueous environment. Examples include glass fibers, polyolefin fibers, particularly polypropylene and polyethylene microfibers, aramid fibers, a fluorinated polymer, particularly, polytetrafluoroethylene fibers, and natural cellulosic fibers. Mixtures of fibers can be used, which may be active or inactive toward binding of target molecules. Preferably, the fibril matrix forms a web that is at least 15 microns, and no greater than 1 millimeter, and more preferably, no greater than 500 microns thick.

If used, the particles are typically insoluble in an aqueous environment. They can be made of one material or a combination of materials, such as in a coated particle. They can be swellable or nonswellable. They can be chosen for their affinity for the target molecules. Examples of some water swellable particles are described in U.S. Pat. No. 4,565,663 (Errede et al.), U.S. Pat. No. 4,460,642 (Errede et al.), and U.S. Pat. No. 4,373,519 (Errede et al.). Particles that are nonswellable in water are described in U.S. Pat. No. 4,810,381 (Hagen et al.), U.S. Pat. No. 4,906,378 (Hagen et al.), U.S. Pat. No. 4,971,736 (Hagen et al.); and U.S. Pat. No. 5,279,742 (Markell et al.). Mixtures of particles can be used, which may be active or inactive toward binding of target molecules.

If coated particles are used, the coating is preferably an aqueous- or organic-insoluble material. The coating may or may not be one to which target molecules, such as proteins, will adhere. Thus, the base particle that is coated can be inorganic or organic. The base particles can include inorganic oxides such as silica, alumina, titania, zirconia, etc., to which are covalently bonded organic groups.

Examples of suitable solid phase materials that include a fibril matrix are described in U.S. Pat. No. 5,279,742 (Markell et al.), U.S. Pat. No. 4,906,378 (Hagen et al.), U.S. Pat. No. 4,153,661 (Ree et al.), U.S. Pat. No. 5,071,610 (Hagen et al.), U.S. Pat. No. 5,147,539 (Hagen et al.), U.S. Pat. No. 5,207,915 (Hagen et al.), and U.S. Pat. No. 5,238,621 (Hagen et al.).

Those that include a polytetrafluoroethylene matrix (PTFE) are particularly preferred. For example, U.S. Pat. No. RE 36,811 (Markell et al.) discloses a solid phase extraction medium that includes: a PTFE fibril matrix, and sorptive particles enmeshed in the matrix, wherein the particles include more than 30 and up to 100 weight percent of porous organic particles, and less than 70 to 0 weight percent of porous (organic-coated or uncoated) inorganic particles, the ratio of sorptive particles to PTFE being in the range of 40:1 to 1:4 by weight.

Particularly preferred solid phase materials are available under the trade designation EMPORE from the 3M Company, St. Paul, Minn. The fundamental basis of the EMPORE technology is the ability to create a particle-loaded membrane, or disk, using any sorbent particle. The particles are tightly held together within an inert matrix of polytetrafluoroethylene (typically 90% sorbent: 10% PTFE, by weight). The PTFE fibrils do not substantially interfere with the activity of the particles. The EMPORE membrane fabrication process results in a denser, more uniform extraction medium than can be achieved in a traditional Solid Phase Extraction (SPE) column or cartridge prepared with the same size particles.

In another preferred embodiment, the solid phase material (e.g., a microporous thermoplastic polymeric support) has a microporous structure characterized by a multiplicity of spaced, randomly dispersed, nonuniform shaped, equiaxed particles of thermoplastic polymer connected by fibrils. Particles are spaced from one another to provide a network of micropores therebetween. Particles are connected to each other by fibrils, which radiate from each particle to the adjacent particles. Either, or both, the particles or fibrils may be hydrophobic. Examples of such preferred materials have a high surface area, often as high as 40 meters$^2$/gram as measured by Hg surface area techniques and pore sizes up to 5 microns.

This type of fibrous material can be made by a preferred technique that involves the use of induced phase separation. This involves melt blending a thermoplastic polymer with an immiscible liquid at a temperature sufficient to form a homogeneous mixture, forming an article from the solution into the desired shape, cooling the shaped article so as to induce phase separation of the liquid and the polymer, and to ultimately solidify the polymer and remove a substantial portion of the liquid leaving a microporous polymer matrix. This method and the preferred materials are described in detail in U.S. Pat. No. 4,726,989 (Mrozinski), U.S. Pat. No. 4,957,943 (McAllister et al.), and U.S. Pat. No. 4,539,256 (Shipman). Such materials are referred to as thermally induced phase separation membranes (TIPS membranes) and are particularly preferred.

Other suitable solid phase materials include nonwoven materials as disclosed in U.S. Pat. No. 5,328,758 (Markell et al.). This material includes a compressed or fused particulate-containing nonwoven web (preferably blown microfibrous) that includes high sorptive-efficiency chromatographic grade particles.

Other suitable solid phase materials include those known as HIPE Foams, which are described, for example, in U.S. Pat. Pub. No. 2003/0011092 (Tan et al.). "HIPE" or "high internal phase emulsion" means an emulsion that includes a continuous reactive phase, typically an oil phase, and a discontinuous or co-continuous phase immiscible with the oil phase, typically a water phase, wherein the immiscible phase includes at least 74 volume percent of the emulsion. Many polymeric foams made from HIPE's are typically relatively open-celled. This means that most or all of the cells are in unobstructed communication with adjoining cells. The cells in such substantially open-celled foam structures have intercellular windows that are typically large enough to permit fluid transfer from one cell to another within the foam structure.

Preferably, the solid phase material includes functional groups that bind target molecules. For example, in one preferred embodiment, the solid phase material will have reactive functional groups or be treated to have reactive functional groups that are capable of forming covalent bonds with ligand molecules or groups of ligand molecules. These covalently bonded ligand molecules, which form the capture sites in certain embodiments of the invention, will bind target molecules from samples. For example, U.S. Pat. No. 5,999,935 (Rasmussen et al.) discloses a solid phase material that includes: covalently reactive particles incorporated within a continuous, porous matrix, said reactive particles having surfaces that includes covalently reactive functional groups capable of directly forming covalent chemical bonds with nucleophilic ligands without need for an intermediate activation step.

In this context, examples of solid phase materials may be solid phase materials containing any one of several commercially available beads with reactive chemistries such as EMPHAZE (3M Company, Saint Paul, Minn.). Ligands such as polypeptides, nucleic acids, small molecules may be coupled covalently to these solid phase materials using procedures supplied by the manufacturers of the beads.

The capture sites can also be provided by hydrophobically attached molecules. These include, for example, proteins such as those used in affinity chemistries. These include, but are not limited to, Protein A, Protein G, avidin, streptavidin, lectins such as jacaline and concanavolin A, antibodies, and receptor proteins. Other capture sites include, but are not limited to, metal affinity ligands, boronates, protein binding dyes such as Cibacron Blue 3GA, polypeptides, Protein A mimetics, and oligonucleotides. Such capture molecules can be added to the solid phase material in a variety of ways. Typically, they are added by saturating the solid phase material with an aqueous solution of the capture molecules, which may include a variety of salt concentrations.

Various combinations or mixtures of capture sites can be incorporated into a solid phase material.

Surfactants

The nonspecific binding of molecules to a solid phase material is decreased by treatment with a nonionic fluorinated surfactant. The fluorinated surfactant includes two or more fluorinated hydrophobic segments and one or more hydrophilic segments.

In this context, a hydrophobic segment is defined as one that preferentially orients itself within the organic phase at the water-organic interface of a dispersion of the surfactant in a water-organic two-phase mixture. A hydrophilic segment is defined as one that orients itself within the water phase in the above system.

The surfactant can be applied using an aqueous solution of the surfactant, although organic solvents can be used if desired. The surfactant can be applied neat or as a solution or dispersion, which can be in a wide range of concentrations. The surfactant can be applied using coating techniques such as dipping, flow-through coating, knife coating, etc.

After application of the surfactant, the surface is typically washed to remove excess surfactant, but surprisingly this still provides beneficial results. Although it is not necessarily a limitation of the invention, it is believed that this results in the surfactant forming a monolayer on the solid phase material. Alternatively, the surfactant can be applied to a solid phase material and dried, thereby forming a thicker layer.

Exemplary fluorinated surfactants (i.e., fluorosurfactants) include those available under the trade designation ZONYL from DuPont (Wilmington, Del.), such as ZONYL FSN, FSN-100, FSO-100, and FSO-300, which are fluoro-polyoxyethylene surfactants, and NOVEC FC4432 and FC4430 from 3M Company (St. Paul, Minn.). The fluorosurfactants appear to coat the surface of the solid phase material thereby preventing binding of other materials.

Other exemplary, and preferred, fluorinated surfactants are derived from nonafluorobutanesulfonyl fluoride that contains polyalkyleneoxy side chains and may be copolymerized with acrylic acid or methacrylic acid to form polyacrylates or polymethacrylates. Specific examples are disclosed, for example, in U.S. Pat. Publication No. 2003/0139550 (Savu et al.) and U.S. Pat. Publication No. 2003/0139549 (Savu et al.).

Such fluorinated surfactants include at least one unit of the following formula (I):

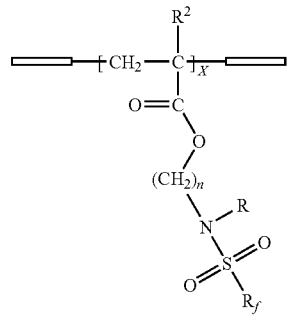

wherein: the rectangular box represents a bond in a polymerizable or polymer chain; $R_f$ is a (C3-C10) linear or branched perfluorinated group (preferably, a linear group, and more preferably a $-C_4F_9$ group); R and $R^2$ are each independently hydrogen or a C1-C4 alkyl group (preferably, hydrogen or methyl); n is an integer of 2 to 10 (preferably, n=2-3, and more preferably, n=2); and x is at least 1.

Preferably, such fluorinated surfactants are of the following formula (II):

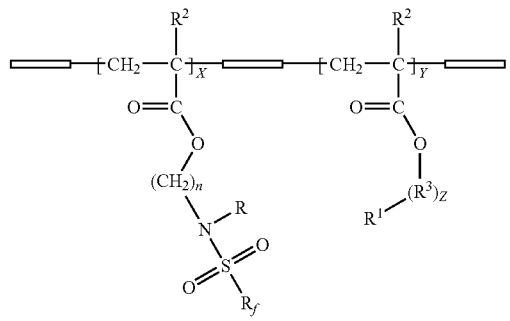

wherein: the rectangular box represents a bond in a polymerizable or polymer chain; R, $R^1$, and $R^2$ are each independently hydrogen or a C1-C4 alkyl group (preferably, hydrogen or methyl); n is an integer of 2 to 10 (preferably, n=2-3, and more preferably, n=2); $R^3$ is a straight or branched alkylene-oxy group, linked together and having 2-6 carbon atoms, or a straight or branched alkylene group having 12-20 carbon atoms; and x, y, and z are each independently at least 1.

In certain embodiments, $R^3$ of the surfactant of Formula II is a group of the formula $(EO)_p-(PO)_q-(EO)_p$ or $(PO)_q-(EO)_p-(PO)_q$. In certain embodiments, p is an integer of 1 to 128 and q is an integer of 0 to 54.

In certain embodiments, $R^3$ of the surfactant of Formula II is of the formula $(PO)_q-(EO)_p-(PO)_q$. In certain embodiments, R and $R^1$ are methyl, q is 0, and p is 4 to 10. In certain embodiments, q is 9 to 22 and p is 14 to 164.

In certain embodiments, $R^3$ of the surfactant of Formula II is of the formula $(EO)_p-(PO)_q-(EO)_p$. In certain embodiments, p is an integer of 7 to 128 and q is an integer of 21 to 54. In certain embodiments, p is 11 and q is 21.

Optional Secondary Blocking Agents

Optional secondary blocking agents include those conventionally used in ELISA assays, immunoblotting, etc. Examples include polypeptides, particularly proteins, such as casein, fetal calf serum, bovine serum albumin, lipid binding protein, and the like. They also include nucleic acids, such as polyA, herring DNA, salmon sperm DNA, and the like. They also include surfactants, stabilizing agents, lipids, and biological solutions such as milk. Various combinations of secondary blocking agents can be used if desired.

These could be used in amounts conventionally used in, for example, ELISA assays, immunoblotting, etc. For example, secondary blocking agents (e.g., nonfat dry milk, BSA, TWEEN 20) can be applied from, for example, a 5 wt-% of nonfat dry milk solution, a 3 wt-% BSA solution, or a 0.2 wt-% TWEEN 20 solution.

The blocking agent can be added before the surfactant or simultaneously with the surfactant, but, typically, it is not added after the surfactant.

Samples

The methods of the present invention can be used to isolate target molecules (e.g., biological macromolecules, such as polypeptides and polynucleotides, and small organic molecules) from a wide variety of samples, particularly biological samples, such as body fluids (e.g., whole blood, blood serum, urine, saliva, cerebral spinal fluid, semen, or synovial lymphatic fluid), various tissues (e.g., skin, hair, fur, feces, tumors, or organs such as liver or spleen), cell cultures or cell culture supernatants, etc. The sample can be a food sample, a beverage sample, a fermentation broth, a clinical sample used to diagnose, treat, monitor, or cure a disease or disorder, a forensic sample, or an agricultural sample (e.g., from a plant or animal), or an environmental sample (e.g., soil, dirt, or garbage).

Biological samples are those of biological or biochemical origin. Those suitable for use in the methods of the present invention can be derived from mammalian, plant, bacterial, or yeast sources. The biological sample can be in the form of single cells, in the form of a tissue, or fluids of biologic origin. Cells or tissue can be derived from in vitro culture. Significantly, certain embodiments of the invention use whole blood without any preprocessing (e.g., lysing, filtering, etc.). Alternatively, whole blood can be preprocessed and the fractions used as the sample in the methods of the invention.

The sample can be a solid sample (e.g., solid tissue) that is dissolved or dispersed in water or an organic medium. For example, the sample can be an organ homogenate (e.g., liver, spleen).

The type of sample is not a limitation of the present invention.

The isolated target molecules (e.g., polypeptides, DNA, or RNA) can be used, preferably without further purification or washing, for a wide variety of applications. For example, polypeptides can be used in the quantification of target molecules in samples, qualitative identification of immuno-complexes formed with the ligand molecules, testing activity of coupled ligand, and the like. For example, nucleic acids can be used for amplification, sequencing, labeling, annealing, restriction digest, ligation, reverse transcriptase, hybridization, Southern blot, Northern blot, and the like.

The target molecules may be isolated according to the invention from an impure, partially pure, or a pure sample. The purity of the original sample is not critical, as target molecules may be isolated from even grossly impure samples. If an original sample of higher purity is desired, the sample may be treated according to any conventional means known to those of skill in the art prior to undergoing the methods of the present invention. For example, the sample may be processed so as to remove certain impurities such as insoluble materials prior to subjecting the sample to a method of the present invention.

The target molecules may be polypeptides, polynucleotides (i.e., nucleic acid), or small organic molecules. The target molecules may be of any molecular weight. For example, polypeptides may be from a few amino acids long to thousands of amino acids long, large and small intact proteins with post-expression modifications, modified polypeptides with any number and size of chemical modifications and functional groups.

The sample containing the target molecules may be in a wide variety of volumes. For example, the applied volume may be as large as 1 liter or as small as 1 µL, or even less. The sample size typically varies depending on the desired application and equipment.

The amount of target material that can be removed from the solid phase material according to the methods of the present invention is more than can be removed when a fluorinated nonionic surfactant is not used. The amount of target material that can be removed from the solid phase material treated with a fluorinated nonionic surfactant is preferably in an amount of at least 50%, more preferably at least 70%, even more preferably at least 90%, and even more preferably at least 98%, of the adhered target molecules.

Elution Techniques

The adhered target molecules can be eluted using a variety of eluting reagents. Such eluting reagents can include buffers, surfactants (which can be cationic, anionic, nonionic, or zwitterionic), acidic solutions, basic solutions, and solutions containing high concentrations of salts (such as sodium chloride or sodium sulfate, etc.). Advantageously and surprisingly, the adhered target molecules can be removed simply by changing pH and/or ionic strength, or by adding a denaturant. Typically, the eluting reagent is one that does not disrupt hydrogen bonding. Thus, generally, organic solvents are not used as the eluting reagents.

Examples of suitable elution buffers include glycine-acetic acid, trifluoroacetic acid, N-[2-Hydroxyethyl]piperazine-N'-[2-ethanesulfonic acid] (HEPES), 3-[N-Morpholino]propanesulfonic acid (MOPS), piperazine-N,N'-bis[2-ethanesulfonic acid] (PIPES), 2-[N-Morpholino]ethanesulfonic acid (MES), TRIS-EDTA (TE) buffer, sodium citrate, ammonium acetate, carbonate salts, and bicarbonates, etc. Various combinations of such materials can be used. The concentration of an elution buffer in an eluting reagent can be readily determined by one of skill in the art.

The amount of eluting reagent used depends on several factors including desired recovery of captured target, format of device in which method is carried out, maximum tolerable dilution of target, etc. Typically, the recovery of the captured target increases with increasing amounts of elution reagent and then tapers off for further elutions. Device formats (such as microfluidic devices) may limit the amount of elution reagent used due to space limitations. Using excess elution reagent will result in dilution of the target. There may be practical limits to the tolerable target dilution before it becomes unusable in steps subsequent to the purification described in these methods. For example, dilute solutions may need to be concentrated before subsequent steps and this may or may not be possible due to time and equipment limitations.

Devices and Kits

The method of the invention can be conducted in filtration devices which facilitate the movement of solutions through solid phase materials (referred to as flow-through devices) by means including centrifugation, suction, or pressure. Other devices include microtiter plates and microfluidic devices.

Although the methods can be used in a variety of devices, a variety of illustrative embodiments of microtiter devices are described in U.S. Pat. No. 5,264,184 (Aysta et al.), U.S. Pat. No. 5,464,541 (Aysta et al.), and U.S. Pat. No. 5,620,663 (Aysta et al.), and in U.S. Pat. Publication Nos. 2003/0080454 and 2003/0155034. A variety of illustrative embodiments of microfluidic devices are described in U.S. Patent Publication No. 2002/0047003 (published Apr. 25, 2003).

The present invention also provides a kit, which can include a solid phase material either with or without a holder (for example, a filter holder such as a syringe filter holder or a spin filter holder, or a column with retaining frits at each end for retaining particulate material), a nonionic fluorinated surfactant (either neat or in a solution), optionally a secondary binding agent, and instructions for use (e.g., for adhering target molecules and optionally eluting such molecules). Preferably, the present invention provides kits that include a flow-through receptacle having a solid phase material therein and a nonionic fluorinated surfactant.

Other components that could be included within kits of the present invention include conventional reagents such as wash solutions, coupling buffers, quenching buffers, blocking buffers, elution buffers, and the like. Other components that could be included within kits of the present invention include conventional equipment such as spin columns, cartridges, 96-well filter plates, syringe filters, collection units, syringes, and the like.

The kits typically include packaging material, which refers to one or more physical structures used to house the contents of the kit. The packaging material can be constructed by well-known methods, preferably to provide a contaminant-free environment. The packaging material may have a label that indicates the contents of the kit. In addition, the kit contains printed instructions indicating how the materials within the kit are employed. As used herein, the term "package" refers to a solid matrix or material such as glass, plastic, paper, foil, and the like.

"Instructions" typically include a tangible expression describing the various methods of the present invention, including, for example, preparation of the solid phase material, the relative amounts of reagents and samples, maintenance time periods, temperature, buffer conditions, and the like.

Applications

Target molecules may be separated from samples using a technique known as affinity purification. In this technique, ligand molecules that interact specifically with the target molecules are identified. These ligand molecules are attached or immobilized (either covalently or non-covalently) to solid phase material which form the affinity purification supports. Such supports may be exposed to blocking agents to block open adsorption sites. Samples are allowed to interact with the ligand molecules on the solid phase materials wherein some of the target molecules in the sample bind to the ligands. These bound target molecules are retained on the solid phase material when the sample is removed. Further washing may be performed to remove non-target molecules from the solid phase material. Finally some of the bound target molecules are eluted using elution reagents. These purified target molecules are said to be purified by affinity purification.

Groups of target molecules that interact together in specific situations (e.g., inside a cell organelle) may be identified and purified from samples using a technique known as immuno-complex separation or protein-to-protein interaction separations. In this technique, one or multiple ligand molecules that form part of the complex with the target molecules are identified. These ligand molecules are attached or immobilized (either covalently or non-covalently) to solid phase material which form the affinity purification supports. Such supports may be exposed to blocking agents to block open adsorption sites. Samples are allowed to interact with the ligand molecules on the solid phase materials wherein some of the target molecules in the sample bind to the ligands and form complexes. These bound target molecule complexes are retained on the solid phase material when the sample is removed. Further gentle washing may be performed to remove molecules that are not part of these complexes, from the solid phase material. Finally some of the bound target molecule complexes are eluted using elution reagents.

Immuno-complex capture or protein-to-protein complex capture can be used in studying the function and association of proteins in biologic systems. The same principles can also be used to study the function and association of other molecules.

Certain embodiments of the present invention, particularly those in which the capture sites are provided by molecules that hydrophobically attach to the solid phase material, such as capture proteins, can be used in protein-based assays such as ELISA's and RIA's. They can be used in medical applications where it is desirable to have a medical device coated with a specific protein (e.g., one that prevents clots from forming), but not have other proteins bind. It might also be desirable to bind a functional protein to a surface but then not allow adsorption of other proteins or other biomolecules that will promote microbial adhesion.

Objects and advantages of this invention are further illustrated by the following examples, but the particular materials and amount thereof recited in these examples, as well as other conditions and details, should not be construed to unduly limit this invention.

EXAMPLES

Example 1

Comparison of Blocking Cocktails Containing Either a Polymeric Fluorinated or a Non-fluorinated Surfactant An EMPHAZE AB1 reactive support loaded perfluoropoly-tetrafluoroethylene (PTFE) membrane was prepared and derivatized with Protein A. This was blocked with a bovine serum albumin solution containing either a polymeric fluorocarbon nonionic surfactant or a nonfluorinated monomeric surfactant. The membrane was then challenged with a solution of radiolabeled human IgG antibody under binding conditions. The membrane was then eluted and the eluate counted to determine the recovery of the IgG.

Membrane Fabrication:

A fibrillated PTFE membrane loaded with EMPHAZE AB1 Reactive Support (3M Co., St. Paul, Minn.) was prepared according to the methods disclosed in U.S. Pat. No. 4,906,378. The final membrane was 90% by weight EMPHAZE AB1 and was about 0.8 mm thick. For use in this experiment test cartridges were prepared by securing 1.26 cm diameter disks of the membrane in the bottom of 6 mL polypropylene syringe barrels using friction fit polypropylene retainer rings.

Preparation of I-125 Labeled IgG:

Human IgG protein antibody (No. 009-0102, Rockland Co., Gilbertsville, Pa.) was labeled with radioactive iodine (I-125) using the method of Fraker and Speck (*Biochem Biophys. Res. Commun.*, 80, 849-857 (1978)).

Buffers:
Binding buffer: 0.10 M sodium phosphate with 0.9 M sodium sulfate at pH 7.5
Washing buffer: Phosphate Buffered Saline (No. 28372, Pierce, Rockford, Ill.)
Quenching buffer: 3.0M ethanolamine at pH 9.5
Blocking buffer: 0.1% bovine serum albumin in washing buffer with either 0.1% TRITON X-100 nonionic surfactant (Sigma Co., St. Louis, Mo.) or 0.1% FC 4432 polymeric fluorocarbon surfactant (3M Co., St. Paul, Minn.)
Elution buffer: 0.1M Glycine with 2% acetic acid at pH 2.0

Procedure:
1. A 0.5-mL sample of a 1.5 mg/mL Protein A (No. rPA50, RepliGen Corp., Waltham, Mass.) solution in the binding buffer was added to the cartridges, incubated at room temperature for 30 minutes, and then drawn through the membranes using vacuum.
2. The cartridges were then washed with 1 mL of binding buffer followed by 2 mL of washing buffer.
3. Two (2.0) mL of the quenching buffer was then drawn through the membranes. A second 2.0 mL of quenching buffer was added incubated for two hours and then drawn through. The cartridges were then washed with 12 mL of washing buffer.
4. Two (2.0) mL of the blocking buffer was drawn through the cartridges and a second 2.0-mL aliquot added, incubated for one hour and then drawn through the membranes.
5. The cartridges were then washed with 15 mL of the washing buffer.
6. A 0.4-mL sample containing 10 micrograms of I-125 labeled human IgG in washing buffer was added to the cartridges and incubated for 15 minutes. It was then drawn through and the cartridges washed with 2 mL of the washing buffer. The washing step was repeated.
7. The labeled IgG was then eluted with two separate 2-mL aliquots of the elution buffer.

All fractions from this experiment as well as the membranes were retained and counted to determine the fate of the I-125 labeled IgG sample.

Results:
Table 1 shows that using the nonionic polymeric fluorocarbon surfactant (NOVEC FC4432) resulted in a significantly higher recovery of the IgG.

TABLE 1

| Blocking buffer | % IgG bound | % bound IgG that is eluted |
|---|---|---|
| 0.1% bovine serum albumin with 0.1% TRITON X-100 | 83 | 10 |
| 0.1% bovine serum albumin with 0.1% NOVEC FC4432 fluorosurfactant | 63 | 95 |

Example 2

Blocking With a Nonionic Polymeric Fluorocarbon Surfactant to Improve Protein Recovery from a Complex Biological Fluid I-125 labeled is spiked into a complex biological fluid and then bound to and eluted from an EMPHAZE AB1 loaded PTFE membrane that has been derivatized with Protein A.

Membrane:
A membrane fabricated as described in Experiment 1 was used except it was formed into 0.77 cm disks and secured in the bottom of the wells of a 96 well polypropylene flow through plate (as disclosed in U.S. Pat. No. 5,264,184 (Aysta et al.), U.S. Pat. No. 5,464,541 (Aysta et al.), and U.S. Pat. No. 5,620,663 (Aysta et al.)) by polypropylene retainer rings. Solutions were drawn through the membrane by centrifugal force using a plate centrifuge.

Procedure:
All reagents and buffers used were the same prepared as in Experiment 1 except that in place of the binding buffer the labeled IgG was dissolved in X-VIVO-20 Growth Medium (Cambrex Bio Science Walkersville, Inc., East Rutherford, N.J.) and the blocking buffer was either 0.1% NOVEC FC4432 in washing buffer or just washing buffer. All eluates and membranes were collected and counted to determine the fate of the I-125 IgG.
1. A 0.166-mL aliquot of binding buffer containing 500 micrograms of Protein A was pipetted into the wells of the plate and incubated for 30 minutes. This solution was then centrifuged out and into a collection plate.
2. The wells were then washed with 0.8 mL of washing buffer.
3. A 0.7-mL aliquot of quenching buffer was pipetted into each well and centrifuged out. A second 0.7-mL aliquot was added to each well and the plate incubated for two hours. This solution was centrifuged out and the wells washed with four aliquots of 0.8 mL of washing buffer.
4. A 0.7-mL aliquot of the blocking buffer or the washing buffer was added to each well and then centrifuged out.
5. The wells were then washed with four 1-mL aliquots of the washing buffer.
6. A 0.135-mL aliquot of the X-VIVO-20 Growth Medium containing 10 micrograms of I-125 labeled IgG was added to each well and the plate incubated for 15 minutes. The plate was then centrifuged to remove the sample and washed with 0.5 mL of washing buffer.
7. The IgG was then eluted using two 0.3-mL aliquots of elution buffer Results:
Table 2 shows that blocking with NOVEC FC4432 fluorosurfactant significantly increases the recovery of the IgG.

TABLE 2

| Blocking | % of IgG bound | % of bound IgG that is eluted |
|---|---|---|
| No blocking | 73.5 | 20 |
| NOVEC FC4432 fluorosurfactant blocking | 66 | 93 |

Example 3

Comparison of Blocking Using a Nonionic Polymeric Fluorosurfactant and a Nonionic Monomeric Surfactant The effect of treatment by either a nonionic polymeric fluorosurfactant or nonionic monomeric fluorosurfactant on the resistance to protein adsorption of a polypropylene loaded fibrillated PTFE membrane was determined by treating the membrane and then challenging with a fluorescein tagged protein.

Membrane:

A polypropylene particle loaded fibrillated PTFE membrane was fabricated as described in using polypropylene powder (No. 140S, Micropowders, Inc., Tarrytown, N.Y.). The membrane contained about 90% by weight polypropylene and was approximately 0.8 mm thick. For this experiment, it was cut into 0.77-cm diameter disks and secured by polypropylene retainer rings to the bottom of empty 2.1-cm polypropylene chromatography columns. Vacuum was used to draw solutions through the membrane.

Reagents:

Washing buffer: Phosphate Buffered Saline (No. 28372, Pierce Inc., Rockford, Ill.)

Fluorescein labeled IgG: IgG-FITC (No. F9636, Sigma Co., St. Louis, Mo.) 100 micrograms/mL in washing buffer Nonionic polymeric fluorosurfactant: 0.1% NOVEC FC4430 fluorosurfactant in washing buffer Nonionic monomeric fluorosurfactant: 0.1% ZONYL FSG fluorosurfactant (E.I. duPont deNemours & Co., Willmington, Del.) in washing buffer Procedure:
1. The membrane was wet with methanol and washed with 0.75 mL of washing buffer.
2. The membrane was treated with 0.75 mL of the surfactant or 0.75 mL of washing buffer in the case of the untreated membrane.
3. Thirty (30) mL of the washing buffer was drawn through the membrane.
4. The membrane was challenged by passing 0.2 mL of the fluorescein labeled IgG solution through it.
5. The membrane was washed with two 0.75-mL aliquots of washing buffer.
6. Membranes were examined for fluorescence using a Leica MZFL III fluorescence stereomicroscope with a fluorescein filter set.

Results:

The untreated and the ZONYL FSG nonionic monomeric fluorosurfactant treated membranes were highly fluorescent indicating the fluorescein labeled protein was adsorbed to it and could not be washed off by the washing buffer. The NOVEC FC4430 nonionic polymeric fluorosurfactant treated membrane showed no fluorescence, indicating that it had not adsorbed protein.

Example 4

Use of Nonionic Polymeric Fluorocarbon Surfactant as a Blocking Agent for Affinity Solid Phase Extraction This experiment illustrates that a nonionic polymeric fluorocarbon surfactant can be used as a blocking agent in an affinity extraction in which the affinity ligand is bound to a solid support by hydrophobic interaction only.

Reagents:

The polypropylene membrane in 2.1-cm chromatography columns, fluorescein labeled IgG solution (IgG-FITC), nonionic polymeric fluorocarbon surfactant solution (FC4430) and washing buffer (WB) were the same as used in Example 3. Protein A (rPA50, Repligen Corp., Waltham, Mass.) solution was prepared at 3 mg/mL in a 35 mM CHES buffer at pH 9.0 containing 1M sodium sulfate. The elution buffer (EB) was the same as used in Example 1.

Procedure:

Four polypropylene membranes in the empty columns were fitted to a vacuum manifold and washed with 0.75 mL of methanol followed by 0.75 mL of water. Membranes 1 and 2 were not treated with the Protein A solution. They were treated with 0.3 mL of the CHES/sulfate buffer in which the Protein A was dissolved. Membranes 3 and 4 were then treated with 0.3 mL of the Protein A solution. The membranes were then treated with the solutions summarized in Table 3. Aliquots (0.75 mL) of each solution were used except that 0.2 mL aliquots were used for the fluorescein labeled IgG (IgG-FITC) solution.

TABLE 3

| Membrane 1 (No Protein A) | Membrane 2 (No Protein A) | Membrane 3 (Protein A treated) | Membrane 4 (Protein A treated) |
|---|---|---|---|
| WB | WB | WB | WB |
| WB | WB | WB | WB |
| WB | FC4430 | FC4430 | FC4430 |
| WB | WB | WB | WB |
| WB | WB | WB | WB |
| IgG-FITC | IgG-FITC | IgG-FITC | IgG-FITC |
| WB | WB | WB | WB |
| WB | WB | WB | WB |
| EB | — | — | EB |
| EB | — | — | EB |

The three membranes were then examined for fluorescence by the method detailed in Example 3.

Results:

Membrane 1 was not treated with Protein A or the FC4430. It showed a marked fluorescence indicating that the IgG-FITC was bound and could not be removed with the elution buffer. Membrane 2 was not treated with Protein A but was treated with the FC4430. It showed no fluorescence indicating that no IgG-FITC was bound. Membrane 3 was treated with both the Protein A and the FC4430 but was not eluted. It showed a marked fluorescence indicating that the IgG-FITC was bound. Membrane 4 was treated with both Protein A and FC4430 and was eluted with the elution buffer. It showed no fluorescence indicating that no IgG was bound.

The results indicate that in the absence of Protein A and FC4430 treatments IgG will bind by hydrophobic interaction but will not elute under conditions favorable for Protein A affinity elution (Membrane 1). With only a FC4430 treatment the IgG-FITC will not bind at all (Membrane 2). When treated with Protein A followed by FC4430, the IgG binds as expected (Membrane 3) and can be eluted (Membrane 4).

Thus, the FC4430 does not cause the removal of a protein adsorbed by hydrophobic interaction before treatment but will prevent adsorption after treatment.

The complete disclosures of the patents, patent documents, and publications cited herein are incorporated by reference in their entirety as if each were individually incorporated. Various modifications and alterations to this invention will become apparent to those skilled in the art without departing from the scope of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of reducing non-specific binding of target molecules to a surface, the method comprising:
  providing a sample comprising target molecules;
  providing a solid phase material comprising a surface that comprises a hydrophobic portion and capture sites, wherein the capture sites are either covalently attached or hydrophobically attached to the solid phase material;
  providing a fluorinated nonionic surfactant;
  contacting the solid phase material with the fluorinated nonionic surfactant to block at least a portion of the hydrophobic portion of the solid phase material surface thereby creating a blocked solid phase material;
  contacting the blocked solid phase material with the sample so that at least a portion of the target molecules adheres to the capture sites thereby creating adhered target molecules; and
  optionally removing at least a portion of the adhered target molecules from the blocked solid phase material,
  wherein non-specific binding of target molecules to the surface is decreased relative to non-specific binding to the surface without contacting the solid phase material with the fluorinated nonionic surfactant,
  wherein the fluorinated nonionic surfactant includes at least one unit of the following formula (II):

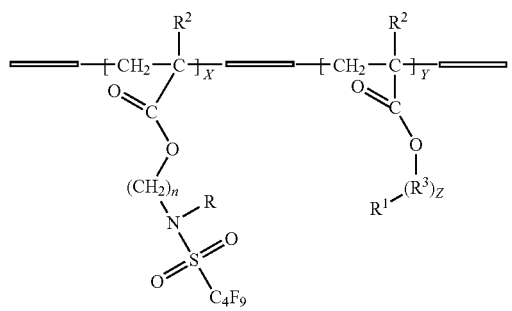

wherein: the rectangular box represents a bond in a polymerizable or polymer chain; R, R$^1$, and R$^2$ are each independently hydrogen or a C1-C4 alkyl group; n is an integer of 2 to 10; R$^3$ is a straight or branched alkylene-oxy group, linked together and having 2-6 carbon atoms, or a straight or branched alkylene group having 12-20 carbon atoms; and x, y, and z are each independently at least 1.

2. The method of claim 1 wherein the solid phase material is porous.

3. The method of claim 2 wherein the solid phase material comprises a polytetrafluoroethylene fibril matrix.

4. The method of claim 1 further comprising contacting the solid phase material with a secondary blocking agent.

5. The method of claim 1 wherein at least 5000 of the adhered target molecules are released upon removing at least a portion of the adhered target molecules from the blocked solid phase material.

6. The method of claim 5 wherein at least 90% of the adhered target molecules are released upon removing at least a portion of the adhered target molecules from the blocked solid phase material.

7. The method of claim 1 wherein providing a solid phase material comprising a surface that comprises a hydrophobic portion and capture sites comprises:
  providing a solid phase material comprising a hydrophobic portion;
  providing a capture protein; and
  contacting solid phase material with the capture protein to hydrophobically attach the capture protein and provide capture sites.

8. The method of claim 7 wherein the capture protein comprises Protein A, Protein G, lectins, antibodies, avidin, streptavidin, receptor proteins, or mixtures thereof.

9. The method of claim 1 wherein the capture sites comprise proteins, metal affinity ligands, boronates, protein binding dyes, polypeptides, Protein A mimetics, oligonucleotides, or mixtures thereof.

10. The method of claim 4 wherein the secondary blocking agent comprises a polypeptide, a nucleic acid, a surfactant, a stabilizing agent, a lipid, a biological sample, or combinations thereof.

11. A method of preparing a solid phase material the method comprising:
  providing a solid phase material comprising a surface that comprises a hydrophobic portion and capture sites, wherein the capture sites are either covalently attached or hydrophobically attached to the solid phase material;
  providing a fluorinated nonionic surfactant; and
  contacting the solid phase material with the fluorinated nonionic surfactant to block at least a portion of the hydrophobic portion,
  wherein the fluorinated nonionic surfactant includes at least one unit of the following formula (II):

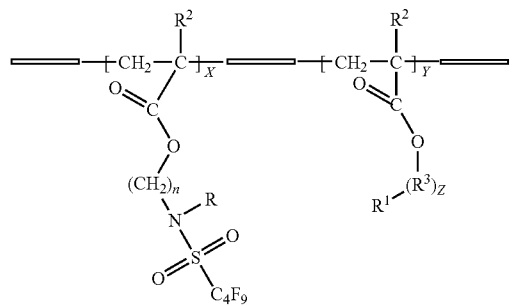

wherein: the rectangular box represents a bond in a polymerizable or polymer chain; R, R$^1$, and R$^2$ are each independently hydrogen or a C1-C4 alkyl group; n is an integer of 2 to 10; R$^3$ is a straight or branched alkylene-oxy group, linked together and having 2-6 carbon atoms, or a straight or branched alkylene group having 12-20 carbon atoms; and x, y, and z are each independently at least 1.

12. The method of claim 11 further comprising contacting the solid phase material with a secondary blocking agent.

13. A method of reducing non-specific binding of target molecules to a surface, the method comprising:

providing a sample comprising target molecules;

providing a solid phase material comprising a hydrophobic portion and one or more hydrophobically attached capture proteins;

providing a fluorinated nonionic;

contacting the solid phase material with the fluorinated nonionic surfactant to block at least a portion of the hydrophobic portion of the solid phase material thereby creating a blocked solid phase material;

contacting the blocked solid phase material with the sample to adhere at least a portion of the target molecules to the one or more capture proteins thereby creating adhered target molecules; and optionally removing at least a portion of the adhered target molecules from the blocked solid phase material, wherein the fluorinated nonionic surfactant includes at least one unit of the following formula (II):

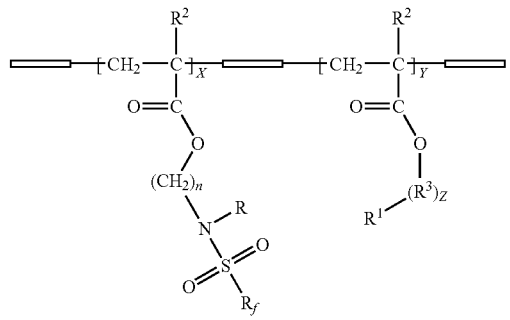

wherein: the rectangular box represents a bond in a polymerizable or polymer chain; R, $R^1$, and $R^2$ are each independently hydrogen or a C1-C4 alkyl group; n is an integer of 2 to 10; $R^3$ is a straight or branched alkylene-oxy group, linked together and having 2-6 carbon atoms, or a straight or branched alkylene group having 12-20 carbon atoms; and x, y, and z are each independently at least 1.

* * * * *

UNITED STATES PATENT AND TRADEMARK OFFICE
CERTIFICATE OF CORRECTION

PATENT NO. : 7,727,710 B2  
APPLICATION NO. : 10/810738  
DATED : June 1, 2010  
INVENTOR(S) : Louis C Haddad It is certified that error appears in the above-identified patent and that said Letters Patent is hereby corrected as shown below:

Title Page 3, Column 1 (Other Publications)
Line 6, delete "Electroophoresis," and insert in place thereof -- Electrophoresis, --.

Title Page 3, Column 2 (Other Publications)
Line 52, delete "Clinincal" and insert in place thereof -- Clinical --.

Title Page 4, Column 1 (Other Publications)
Line 2, delete "pseudopetide" and insert in place thereof -- pseudopeptide --.

Line 19, delete "Flurosurfactants," and insert in place thereof -- Fluorosurfactants --.

Column 4
Line 7, delete "26" and insert in place thereof -- 26, --.

Line 40 (approx.), delete "adherance" and insert in place thereof -- adherence --.

Column 9
Line 18, delete "concanavolin A" and insert in place thereof -- concanavalin A --.

Column 10

Line 40 (approx.), delete " " and insert in place thereof -- --. 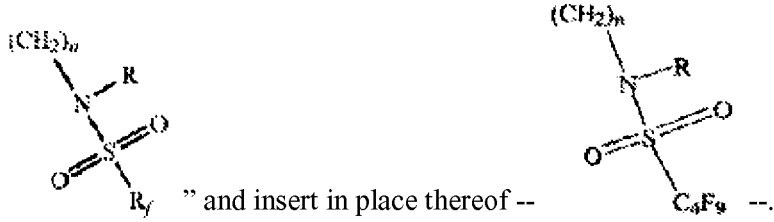

Signed and Sealed this

Nineteenth Day of October, 2010

David J. Kappos
*Director of the United States Patent and Trademark Office*

CERTIFICATE OF CORRECTION (continued)

Column 14
Line 39, delete "amount" and insert in place thereof -- amounts --.

Column 16
Line 52 (approx.), after "buffer" insert -- . --.

Column 19
Line 64, in Claim 5, delete "5000" and insert in place thereof -- 50% --.

Column 22
Line 10 (approx.), delete " 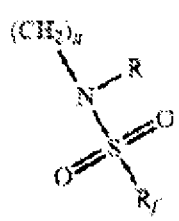 " and insert in place thereof -- 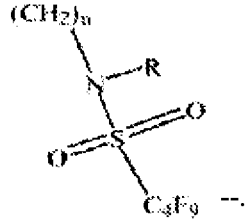 --.